United States Patent [19]
Cyr

[11] Patent Number: 5,987,653
[45] Date of Patent: Nov. 23, 1999

[54] PROTECTIVE EYEWEAR FOR INDUSTRIAL USE

[75] Inventor: Raymond Cyr, Duvernay, Canada

[73] Assignee: Leader Industries Inc., Quebec, Canada

[21] Appl. No.: 09/131,467

[22] Filed: Aug. 10, 1998

[51] Int. Cl.[6] .................................. A61F 9/02; G02C 5/22
[52] U.S. Cl. ................................. 2/448; 2/450; 351/118; 351/119; 351/153; 16/228
[58] Field of Search .................. 2/426, 450, 448, 2/439, 449, 431

[56] References Cited

U.S. PATENT DOCUMENTS

| | | | |
|---|---|---|---|
| 3,544,204 | 12/1970 | Bienenfeld | 351/118 |
| 3,705,761 | 12/1972 | Fujisawa | 351/118 |
| 5,189,447 | 2/1993 | Oleson | 351/121 |
| 5,347,325 | 9/1994 | Lei | 351/118 |
| 5,357,292 | 10/1994 | Wiedner | 351/105 |
| 5,423,092 | 6/1995 | Kawai | 2/441 |
| 5,528,320 | 6/1996 | Specht et al. | 351/106 |
| 5,684,559 | 11/1997 | Lin | 351/110 |
| 5,764,330 | 6/1998 | Simioni | 351/41 |

FOREIGN PATENT DOCUMENTS 614613  8/1947  United Kingdom .

Primary Examiner—John J. Calvert
Assistant Examiner—Tejash D Patel
Attorney, Agent, or Firm—Merchant & Gould, P.C.

[57] ABSTRACT

The eyewear for industrial use comprises a deformable arcuate lens with a pair of temple receiving entries at opposite ends thereof, a deformable brow frame shaped to fit the upper edge of the lens so as to be engageable therewith and a pair of temple pieces, each piece being hingedly connected to a respective opposite end of the brow frame. Assembly of the temple pieces and brow frame to the lens is easily effected by inserting the temple pieces in the entries of the lens and by snap engagement of a mid-section of the brow frame to the upper edge of the lens. The assembly is made of plastic material so that it may be resiliently deformed to adapt to the various sizes of head of users.

4 Claims, 4 Drawing Sheets

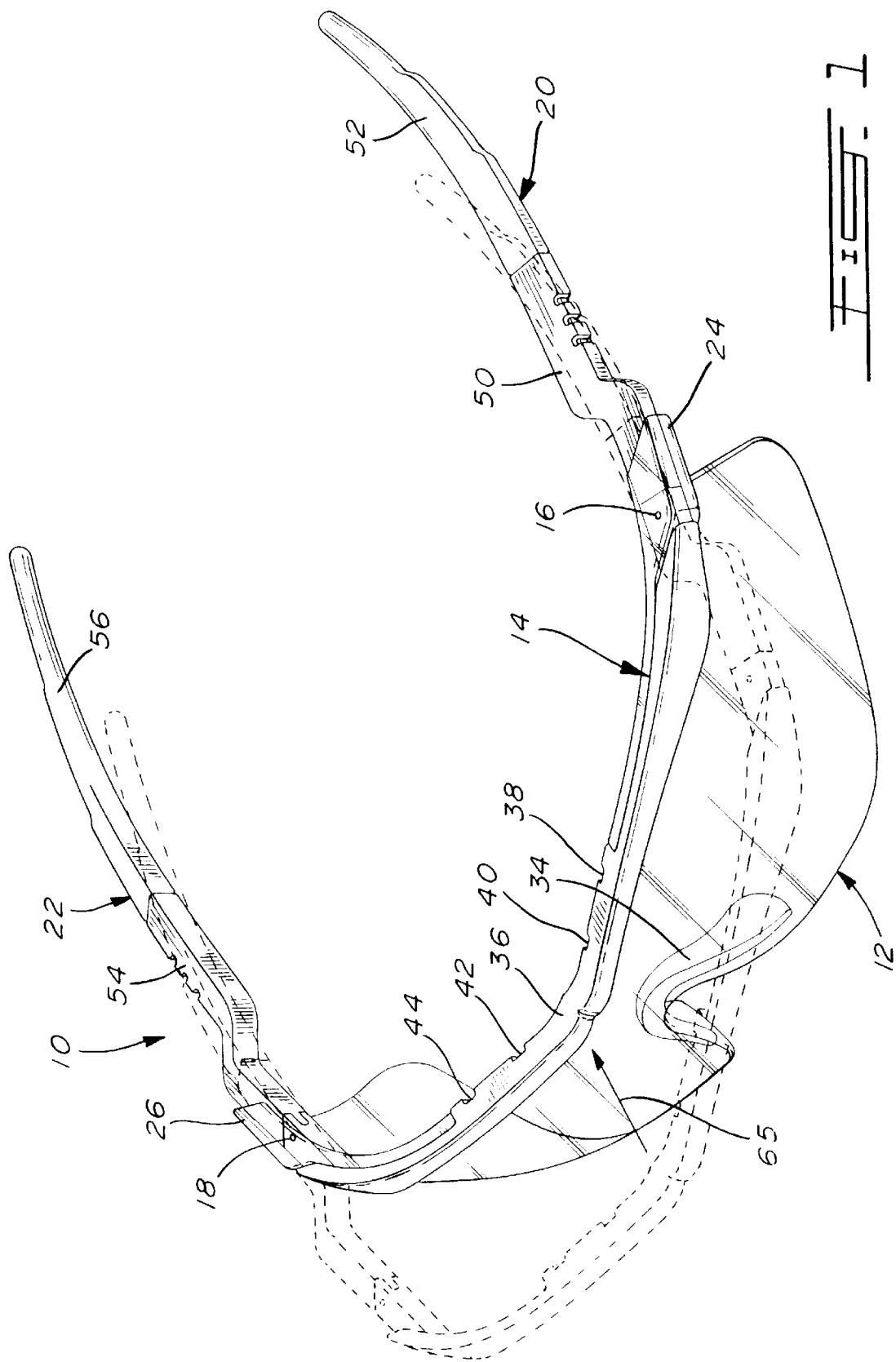

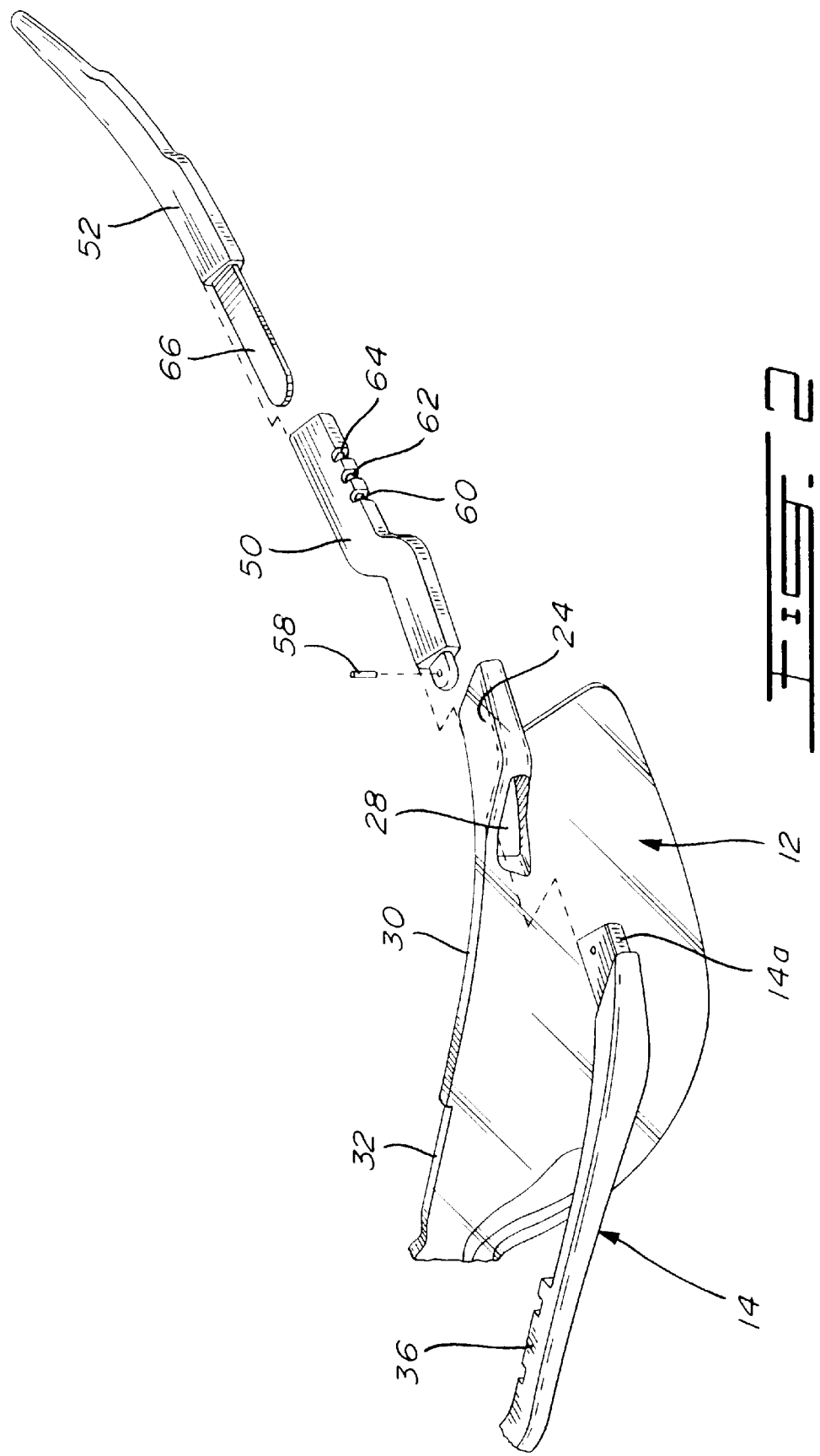

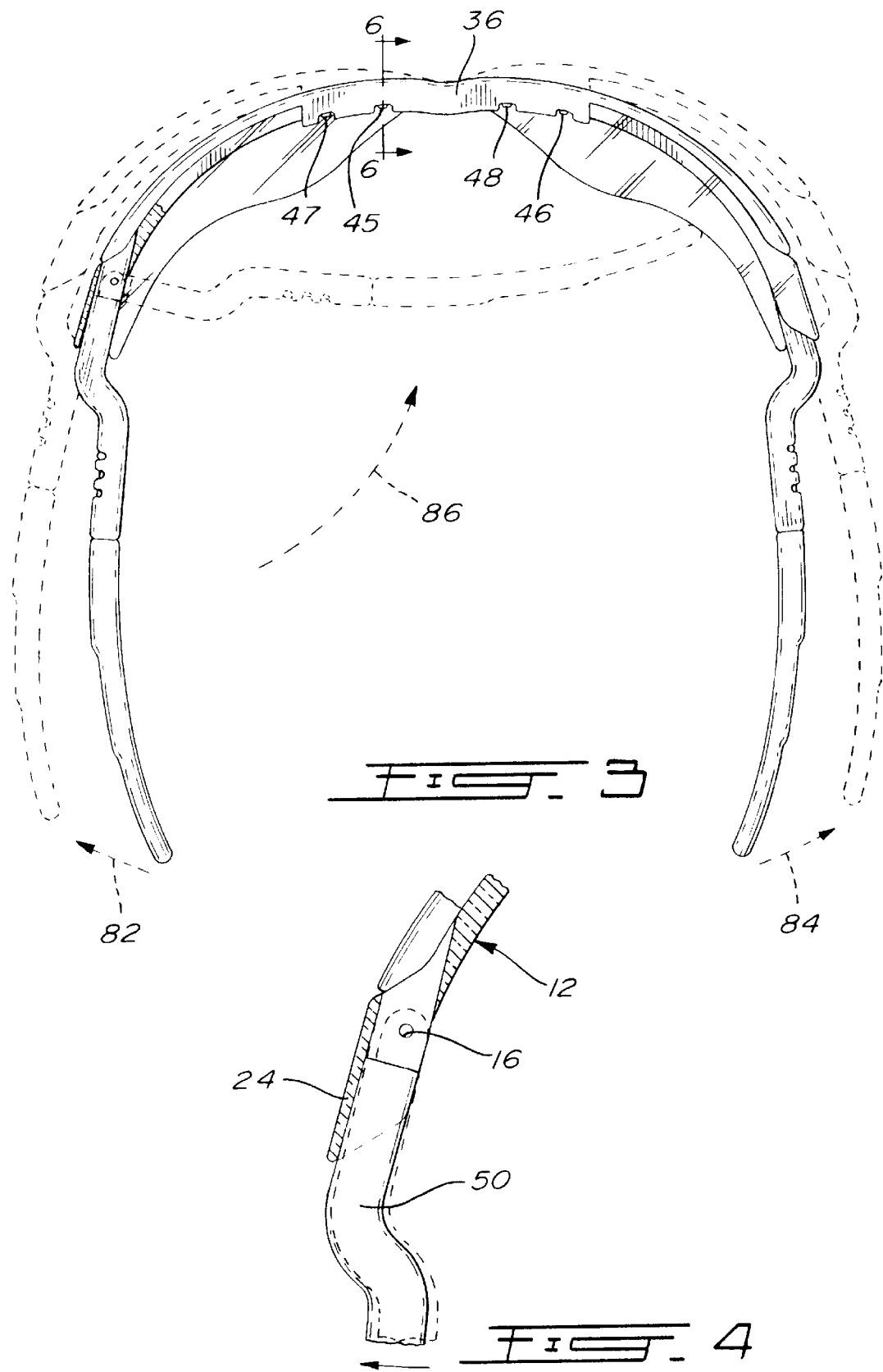

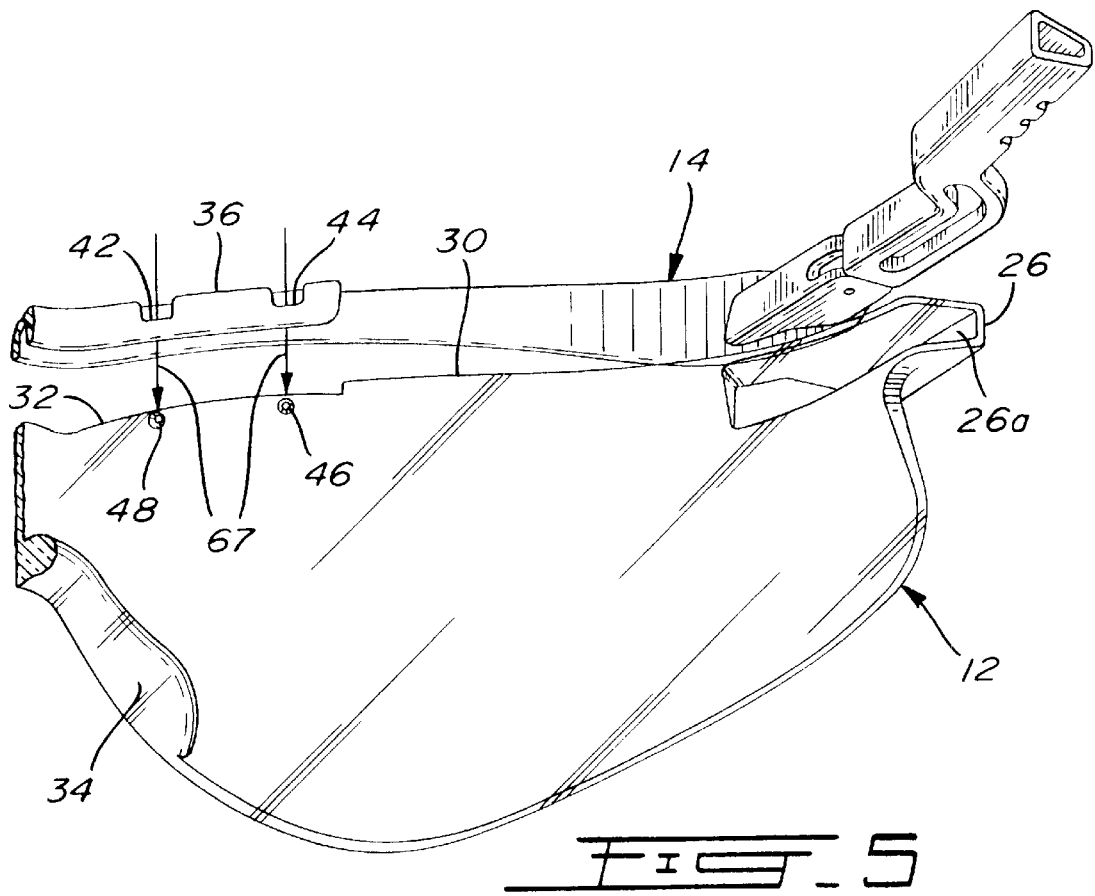
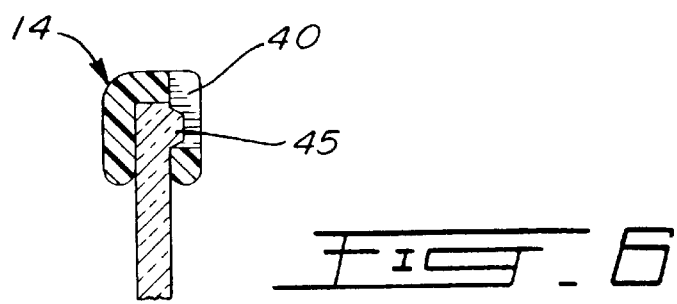

PROTECTIVE EYEWEAR FOR INDUSTRIAL USE

FIELD OF THE INVENTION

The present invention relates to a protective eyewear for industrial use.

BACKGROUND OF THE INVENTION

Often, in industrial use, the lens and/or temples pieces of a protective eyewear often break, requiring the user to discard the entire eyewear and replace it with a new pair.

Another problem in industry has been to provide a standard protective eyewear that can accommodate comfortably different head sizes. On the other hand, it is important to provide the user with appropriate comfort when wearing such eyeglasses and this can hardly be obtained since there are various sizes of user heads.

Thus, there is a need for a protective eyewear for industrial use that can be easily mounted and dismounted in the event of breakage of one of its components and, at the same time, providing comfort to its user.

OBJECTS OF THE INVENTION

It is an object of the present invention to overcome the above problems of presently known eyewear for industrial use by providing one which can be easily assembled and disassembled in event of damage and component replacement and which is adjustable for various head sizes.

SUMMARY OF THE INVENTION

The present invention therefore relates to an eyewear that comprises:
   an arcuate lens made of resilient material, the lens having a pair of temple receiving entries at respective opposite ends of its upper edge;
   a brow frame made of resilient material and shaped to fit the upper edge of the lens, the frame including, at mid-section thereof, attachment means for securing the lens thereto; and
   a pair of temple pieces, each temple piece being hingedly connected to a respective opposite end of the brow frame and being pivotable to move between a folded position and a parallel position; whereby, in the parallel position, secured assembly of the brow frame and the temple pieces is easily effected by inserting the temple pieces through the entries and by engaging the attachment means of the brow-frame to the mid-section of the upper edge of the lens.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

Having thus generally described the invention, reference will now be made to the accompanying drawings showing by way of illustration a preferred embodiment thereof and in which:

FIG. 1 is a perspective view of the eyewear of the present invention with dotted lines showing the manner in which the brow frame and the temple pieces are mounted onto the lens;

FIG. 2 is an exploded fragmentary view of some of the components of the eyewear;

FIG. 3 is a top plan view with dotted lines showing the feature of flexibility of the eyeglass;

FIG. 4 is an enlarged top view of the engagement of the temple piece to the lens;

FIG. 5 is a fragmentary exploded view showing the engagement of the brow frame to the lens; and FIG. 6 is a cross-sectional view taken along lines 6—6 of FIG. 3.

DESCRIPTION OF A PREFERRED EMBODIMENT

As used in the present application, the term protective eyewear is intended to encompass all optical devices that have a purpose of protecting the eye against injury, especially during an industrial use.

Referring to FIG. 1, there is shown an eyewear, generally denoted 10, made in accordance with the present invention and consisting essentially of a lens 12, a brow frame 14 to which is hingedly connected at 16, 18 a pair of temple pieces 20 and 22.

Referring also to FIG. 2, the lens 12 comprises, at opposite ends thereof, hollow extensions 24 and 26 providing entry channels (one of which is shown as 28 in FIG. 2). The upper edge 30 of the lens displays a central undercut recess 32, the function of which will be described further hereinbelow. The lens may also have a nose piece 34.

Referring to FIGS. 1 and 5, the brow frame 14 has a shape to correspond to the upper edge 30 of the lens. It also comprises, in its central area, an inverted U-shaped configuration that includes a series of openings 38, 40, 42 and 44. These openings are aligned with corresponding small projections (being shown as 45, 46, 47 and 48 in FIG. 5) which are horizontally spaced in the central area 32 of the upper edge of the lens and on the inner face thereof.

Referring to FIGS. 1 and 2, the respective temple pieces 20 and 22 each comprise a pair of components 50, 52 and 54, 56. Component 50 is hingedly connected to end 14a of the brow frame by means of a pin 58. Component 50 has also small openings 60, 62, 64, the function of which will be described further hereinbelow. Component 50 is hollow so that it may receive a projecting portion 66 of the ear contacting component 52 of the temple piece.

The above description pertaining to the temple piece 20 and its components 50 and 52 needs not be repeated for temple piece 22 together with its components 54 and 56 since they are identically constructed.

The present invention is concerned with the easy mounting and dismounting of the brow frame and temple pieces from the lens should one of these components be damaged and need to be replaced. The assembly consists in bringing the temple pieces mounted to the brow frame to the lens as indicated by arrow 65 in FIG. 1 and passing the temple pieces 20 and 22 through the channel extensions 24 and 26 of the lens. Once the brow frame 14 extends over the upper edge 30 of the lens, the brow frame is vertically moved as indicated by arrow 67 in FIG. 5. The central portion is forced downwardly over the undercut recess 32 of the lens to provide a locking arrangement between the projections 45, 46, 47, 48 into their respective openings 38, 40, 42 and 44 (see FIG. 6). To disassemble the eyewear, an opposite operation is performed; that is, due to the flexibility of the material of the U-shaped part of the brow frame, projections 45, 46, 47, 48 are snapped out of their engagement with their respective brow openings 38, 40, 42, and 44.

The material of the lens and of the brow frame and temple pieces is a plastic material which allows for the components to be deformed so as to perform the engagement and disengagement operations of the components to one another. Referring to FIG. 3, arrows 82 and 84 indicate that the temple pieces may be moved outwardly in a flexible manner so as to conform to the shape of the head size of a user. Arrow 86 indicates that the temple pieces may be folded rearwardly of the lens in a parallel fashion when the eyewear is not used.

The particular shape of the channel extensions of the lens covers and protects the hinge pins 16 and 18 of the eyewear. Also, each channel defines a bearing surface (see 26a in FIG. 5) against which the temple piece may apply some lateral pressure during assembly and/or use.

Although the invention has been described above with respect with one specific form, it will be evident to a person skilled in the art that it may be modified and refined in various ways. It is therefore wished to have it understood that the present invention should not be limited in scope, except by the terms of the following claims.

I claim:

1. Eyewear, comprising;

an arcuate lens made of resilient material, having an upper edge and a pair of temple pieces receiving entries at respective opposite ends of said upper edge;

a brow frame made of resilient material and shaped to fit said upper edge, said brow frame being made of resilient material and having opposite ends; said brow frame including, at mid-section thereof, attachment means for securing said lens thereto; and a pair of temple pieces, each of said temple pieces being hingedly connected to a respective opposite end of said brow frame and being pivotable to move between a folded position and a parallel position;

said temple pieces, in said parallel position, being insertable through said temple pieces receiving entries, wherein secured assembly of said brow frame and said temple pieces is easily effected by inserting said temple pieces through said entries and by engaging said attachment means of said brow frame to said mid-section of said upper edge of said lens.

2. The eyewear of claim 1, wherein each of said temple pieces receiving entries defines an aperture and a pressure bearing surface, said temple pieces, once located in said apertures, bearing against said surfaces.

3. The eyewear of claim 2, wherein each of said temple pieces consists of a branch portion having one end hingedly connected to said brow frame and an ear piece portion adjustably connected to an opposite end of said branch portion.

4. The eyewear of claim 3, wherein said upper edge of said lens has an undercut slot at mid-section thereof to receive said attachment means of said brow frame.

\* \* \* \* \*